United States Patent
Luchterhandt et al.

(10) Patent No.: US 8,722,760 B2
(45) Date of Patent: May 13, 2014

(54) SELF-ADHESIVE COMPOSITIONS INCLUDING A PLURALITY OF ACIDIC COMPOUNDS

(75) Inventors: Thomas Luchterhandt, Greifenberg (DE); Reinhold Hecht, Kaufering (DE); Markus Watermann, Inning am Ammersee (DE); Steven M. Aasen, Woodbury, MN (US)

(73) Assignees: 3M Innovative Properties Company, St Paul, MN (US); 3M Deutschland GmbH, Neuss (DE)

( * ) Notice: Subject to any disclaimer, the term of this patent is extended or adjusted under 35 U.S.C. 154(b) by 876 days.

(21) Appl. No.: 11/573,423

(22) PCT Filed: Aug. 9, 2005

(86) PCT No.: PCT/US2005/028536
§ 371 (c)(1),
(2), (4) Date: Feb. 8, 2007

(87) PCT Pub. No.: WO2006/020760
PCT Pub. Date: Feb. 23, 2006

(65) Prior Publication Data
US 2007/0248927 A1    Oct. 25, 2007

Related U.S. Application Data

(60) Provisional application No. 60/600,658, filed on Aug. 11, 2004.

(51) Int. Cl.
*A61K 6/083*    (2006.01)
*A61K 6/08*    (2006.01)

(52) U.S. Cl.
USPC ......... 523/118; 523/115; 433/226; 433/228.1

(58) Field of Classification Search
USPC .......... 523/116, 118, 120, 115; 433/9, 228.1, 433/226
See application file for complete search history.

(56) References Cited

U.S. PATENT DOCUMENTS

| | | | |
|---|---|---|---|
| 3,655,605 A | 4/1972 | Smith | |
| 3,797,690 A | 3/1974 | Taylor | |
| 4,016,124 A | 4/1977 | Crisp et al. | |
| 4,054,598 A | 10/1977 | Blum et al. | |
| 4,070,321 A | 1/1978 | Goretta et al. | |
| 4,089,830 A | 5/1978 | Tezuka et al. | |
| 4,143,018 A | 3/1979 | Crisp et al. | |
| 4,204,978 A | 5/1980 | Ibsen et al. | |
| 4,259,075 A | 3/1981 | Yamauchi et al. | |
| 4,259,117 A | 3/1981 | Yamauchi et al. | |
| 4,267,108 A | 5/1981 | Blum et al. | |
| 4,298,738 A | 11/1981 | Lechtken et al. | |
| 4,302,381 A | 11/1981 | Omura et al. | |
| 4,304,734 A | 12/1981 | Jary et al. | |
| 4,324,744 A | 4/1982 | Lechtken et al. | |
| 4,327,039 A | 4/1982 | Blum et al. | |
| 4,342,677 A | 8/1982 | Muramatsu et al. | |
| 4,347,233 A | 8/1982 | Yamauchi et al. | |
| 4,356,296 A | 10/1982 | Griffith et al. | |
| 4,360,605 A | 11/1982 | Schmitt et al. | |
| 4,368,403 A | 1/1983 | Lewis | |
| 4,376,835 A | 3/1983 | Schmitt et al. | |
| 4,383,052 A | 5/1983 | Higo et al. | |
| 4,385,109 A | 5/1983 | Lechtken et al. | |
| 4,407,761 A | 10/1983 | Blum et al. | |
| 4,499,251 A | 2/1985 | Omura et al. | |
| 4,503,169 A | 3/1985 | Randklev | |
| 4,507,407 A | 3/1985 | Kluger | |
| 4,526,728 A | 7/1985 | Finke et al. | |
| 4,537,940 A | 8/1985 | Omura et al. | |
| 4,539,382 A | 9/1985 | Omura et al. | |
| 4,612,384 A | 9/1986 | Omura et al. | |
| 4,621,077 A | 11/1986 | Rosini et al. | |
| 4,642,126 A | 2/1987 | Zador et al. | |
| 4,648,843 A | 3/1987 | Mitra | |
| 4,650,847 A | 3/1987 | Omura et al. | |
| 4,652,274 A | 3/1987 | Boettcher et al. | |
| 4,665,217 A | 5/1987 | Reiners et al. | |
| 4,678,436 A | 7/1987 | Kondo | |
| 4,687,767 A | 8/1987 | Bosies et al. | |
| 4,695,251 A | 9/1987 | Randklev | |
| 4,710,523 A | 12/1987 | Lechtken et al. | |
| 4,719,149 A | 1/1988 | Aasen et al. | |
| 4,737,593 A | 4/1988 | Ellrich et al. | |
| 4,752,338 A | 6/1988 | Reiners et al. | |
| 4,755,620 A | 7/1988 | Iwamoto et al. | |
| 4,792,632 A | 12/1988 | Ellrich et al. | |

(Continued)

FOREIGN PATENT DOCUMENTS

| | | |
|---|---|---|
| DE | 2537463 A1 | 4/1976 |
| DE | 35 36076 A1 | 4/1987 |

(Continued)

OTHER PUBLICATIONS

U.S. Appl. No. 60/494,603, filed Aug. 12, 2003, entitled "Dental Compositions and Methods".
Patent Abstracts of Japan, vol. 009, No. 236 (P-390), Sep. 21, 1985 & JP 60 089752A May 20, 1985.
U.S. Appl. No. 60/586,326, filed Jul. 8, 2004, entitled "Dental Methods, Compositions, and Kits Including Acid-sensitive Dyes".
U.S. Appl. No. 60/600,558, filed Aug. 11, 2004 entitled "Dental Methods, Compositions, and Kits Including Acid-sensitive Dyes".
Banerjee et al., *Ind. Eng. Chem. Res.*, vol. 35, No. 9, pp. 3100-3107 "Polymer Precipitation Using a Micellar Nonsolvent: The Role of Surfactant—Polymer Interactions and the Development of a Microencapsulation Technique", (1996).

(Continued)

*Primary Examiner* — Michael Pepitone

(57) ABSTRACT

The present invention provides self-adhesive compositions that include a plurality of acidic compounds. The self-adhesive compositions are useful for applications including, for example, restoring dental structures and adhering orthodontic appliances to teeth.

26 Claims, No Drawings

(56) References Cited

U.S. PATENT DOCUMENTS

| | | | |
|---|---|---|---|
| 4,814,514 A | 3/1989 | Yokota et al. | |
| 4,816,495 A * | 3/1989 | Blackwell et al. | 522/14 |
| 4,872,936 A | 10/1989 | Engelbrecht | |
| 4,922,007 A | 5/1990 | Kieczykowski et al. | |
| 4,939,283 A | 7/1990 | Yokota et al. | |
| 5,019,651 A | 5/1991 | Kieczykowski | |
| 5,026,902 A | 6/1991 | Fock et al. | |
| 5,055,497 A | 10/1991 | Okada et al. | |
| 5,063,257 A | 11/1991 | Akahane et al. | |
| 5,076,844 A | 12/1991 | Fock et al. | |
| 5,130,347 A | 7/1992 | Mitra | |
| 5,154,762 A | 10/1992 | Mitra et al. | |
| 5,172,809 A | 12/1992 | Jacobs et al. | |
| 5,180,757 A | 1/1993 | Lucey | |
| 5,227,413 A | 7/1993 | Mitra | |
| 5,254,198 A | 10/1993 | Kawashima et al. | |
| 5,256,447 A | 10/1993 | Oxman et al. | |
| 5,324,862 A | 6/1994 | Yokota et al. | |
| 5,332,854 A | 7/1994 | Yokota et al. | |
| 5,338,769 A | 8/1994 | Miyamoto | |
| 5,354,827 A | 10/1994 | Muller et al. | |
| 5,367,002 A | 11/1994 | Huang et al. | |
| 5,501,727 A | 3/1996 | Wang et al. | |
| 5,510,517 A | 4/1996 | Dauer et al. | |
| 5,520,725 A | 5/1996 | Kato et al. | |
| 5,525,648 A | 6/1996 | Aasen et al. | |
| 5,530,038 A | 6/1996 | Yamamoto et al. | |
| 5,545,676 A | 8/1996 | Palazzotto et al. | |
| 5,554,030 A | 9/1996 | Ario et al. | |
| 5,575,645 A | 11/1996 | Jacobs et al. | |
| 5,593,303 A | 1/1997 | Cohen et al. | |
| 5,608,042 A | 3/1997 | Himeno | |
| 5,629,361 A | 5/1997 | Nakabayashi et al. | |
| 5,645,429 A | 7/1997 | Blackwell et al. | |
| 5,648,491 A | 7/1997 | Dauer et al. | |
| 5,658,963 A | 8/1997 | Qian et al. | |
| 5,700,875 A | 12/1997 | Zeng et al. | |
| 5,710,194 A | 1/1998 | Hammesfahr et al. | |
| 5,766,012 A | 6/1998 | Rosembaum et al. | |
| 5,834,532 A | 11/1998 | Yamamoto et al. | |
| 5,856,373 A | 1/1999 | Kaisaki et al. | |
| 5,859,089 A | 1/1999 | Qian | |
| 5,871,360 A | 2/1999 | Kato | |
| 5,919,836 A | 7/1999 | Reinhardt | |
| 5,919,846 A | 7/1999 | Batlaw | |
| 5,925,715 A | 7/1999 | Mitra | |
| 5,962,550 A | 10/1999 | Akahane et al. | |
| 5,965,632 A | 10/1999 | Orlowski et al. | |
| 5,980,253 A | 11/1999 | Oxman et al. | |
| 5,980,868 A | 11/1999 | Homola | |
| 6,004,390 A | 12/1999 | Pflug et al. | |
| 6,030,606 A | 2/2000 | Holmes | |
| 6,050,815 A | 4/2000 | Adam et al. | |
| 6,084,004 A | 7/2000 | Weinmann et al. | |
| 6,089,861 A | 7/2000 | Kelly et al. | |
| 6,126,922 A | 10/2000 | Rozzi et al. | |
| 6,172,131 B1 | 1/2001 | Moszner et al. | |
| 6,174,935 B1 | 1/2001 | Matsunae et al. | |
| 6,187,833 B1 | 2/2001 | Oxman et al. | |
| 6,187,836 B1 | 2/2001 | Oxman et al. | |
| 6,213,767 B1 | 4/2001 | Dixon et al. | |
| 6,217,644 B1 * | 4/2001 | Matsunae et al. | 106/35 |
| 6,251,963 B1 | 6/2001 | Kohler et al. | |
| 6,306,926 B1 | 10/2001 | Bretscher et al. | |
| 6,309,215 B1 | 10/2001 | Phan et al. | |
| 6,331,080 B1 | 12/2001 | Cole et al. | |
| 6,350,839 B2 | 2/2002 | Moszner et al. | |
| 6,355,704 B1 | 3/2002 | Nakatsuka et al. | |
| 6,387,979 B1 | 5/2002 | Hino | |
| 6,387,981 B1 | 5/2002 | Zhang et al. | |
| 6,387,982 B1 | 5/2002 | Blackwell | |
| 6,444,725 B1 | 9/2002 | Trom et al. | |
| 6,458,868 B1 | 10/2002 | Okada et al. | |
| 6,472,454 B1 | 10/2002 | Qian | |
| 6,482,871 B1 | 11/2002 | Aasen et al. | |
| 6,506,816 B1 | 1/2003 | Ario et al. | |
| 6,528,555 B1 | 3/2003 | Nikutowski et al. | |
| 6,565,873 B1 | 5/2003 | Shefer et al. | |
| 6,566,413 B1 | 5/2003 | Weinmann et al. | |
| 6,572,693 B1 | 6/2003 | Wu et al. | |
| 6,575,752 B1 | 6/2003 | Pflug | |
| 6,624,236 B1 | 9/2003 | Bissinger et al. | |
| 6,669,927 B2 | 12/2003 | Trom et al. | |
| 6,691,715 B2 | 2/2004 | Matz et al. | |
| 6,765,036 B2 | 7/2004 | Dede et al. | |
| 6,765,038 B2 | 7/2004 | Mitra | |
| 6,830,450 B2 | 12/2004 | Knopp et al. | |
| 6,869,984 B2 | 3/2005 | Kawashima | |
| 6,905,672 B2 | 6/2005 | Rajaiah | |
| 6,916,858 B2 | 7/2005 | Kojima | |
| 6,939,901 B2 | 9/2005 | Nakatsuka | |
| 6,960,079 B2 | 11/2005 | Brennan et al. | |
| 6,982,288 B2 | 1/2006 | Mitra et al. | |
| 6,994,551 B2 | 2/2006 | Wang et al. | |
| 7,090,722 B2 | 8/2006 | Budd et al. | |
| 7,129,281 B2 | 10/2006 | Fujiwara | |
| 7,134,875 B2 | 11/2006 | Oxman | |
| 7,137,812 B2 | 11/2006 | Cleary | |
| 7,173,074 B2 | 2/2007 | Mitra et al. | |
| 7,186,950 B1 | 3/2007 | Fisher | |
| 7,250,452 B2 | 7/2007 | Falsafi | |
| 7,262,228 B2 | 8/2007 | Oxman | |
| 7,374,420 B2 | 5/2008 | Brennan | |
| 7,452,924 B2 * | 11/2008 | Aasen et al. | 523/116 |
| 7,473,096 B2 | 1/2009 | Cinader, Jr. | |
| 7,541,393 B2 | 6/2009 | Mitra | |
| 7,699,605 B2 | 4/2010 | Aasen et al. | |
| 7,841,464 B2 | 11/2010 | Cinader, Jr. | |
| 7,910,632 B2 | 3/2011 | Cinader, Jr. | |
| 2001/0044513 A1 | 11/2001 | Moszner et al. | |
| 2002/0015682 A1 | 2/2002 | Stangel et al. | |
| 2002/0016384 A1 | 2/2002 | Moszner et al. | |
| 2003/0083398 A1 * | 5/2003 | Kawashima et al. | 523/115 |
| 2003/0087986 A1 | 5/2003 | Mitra | |
| 2003/0134934 A1 * | 7/2003 | Kojima et al. | 523/120 |
| 2003/0166737 A1 | 9/2003 | Dede et al. | |
| 2003/0166740 A1 | 9/2003 | Mitra et al. | |
| 2003/0166816 A1 | 9/2003 | Bissinger et al. | |
| 2003/0181541 A1 | 9/2003 | Wu et al. | |
| 2003/0187092 A1 | 10/2003 | Fujiwara | |
| 2003/0195273 A1 | 10/2003 | Mitra | |
| 2003/0196914 A1 | 10/2003 | Tzou et al. | |
| 2003/0198914 A1 | 10/2003 | Brennan et al. | |
| 2004/0110864 A1 | 6/2004 | Hecht et al. | |
| 2004/0151691 A1 | 8/2004 | Oxman et al. | |
| 2004/0206932 A1 | 10/2004 | Abuelyaman | |
| 2005/0074716 A1 | 4/2005 | Cleary et al. | |
| 2005/0133384 A1 | 6/2005 | Cinader | |
| 2005/0154081 A1 | 7/2005 | Yin | |
| 2005/0175965 A1 | 8/2005 | Aasen et al. | |
| 2005/0175966 A1 | 8/2005 | Falsafi et al. | |
| 2005/0176844 A1 | 8/2005 | Aasen et al. | |
| 2005/0252413 A1 | 11/2005 | Kangas et al. | |
| 2005/0252414 A1 | 11/2005 | Craig et al. | |
| 2005/0256223 A1 | 11/2005 | Kolb et al. | |
| 2005/0277084 A1 | 12/2005 | Cinader et al. | |
| 2006/0030637 A1 | 2/2006 | Mitra | |
| 2006/0069181 A1 | 3/2006 | Thalacker | |
| 2006/0084026 A1 | 4/2006 | Cinader et al. | |
| 2007/0039519 A1 | 2/2007 | Kangas et al. | |
| 2007/0207094 A1 | 9/2007 | Oxman | |
| 2007/0248927 A1 | 10/2007 | Luchterhandt | |
| 2008/0096150 A1 | 4/2008 | Cinader | |
| 2008/0299519 A1 | 12/2008 | Craig et al. | |
| 2009/0011388 A1 | 1/2009 | Craig | |
| 2009/0030101 A1 | 1/2009 | Sang et al. | |
| 2009/0075239 A1 | 3/2009 | Abuelyaman | |

FOREIGN PATENT DOCUMENTS

| | | |
|---|---|---|
| DE | 273 846 A1 | 11/1989 |
| DE | 199 18 974 A1 | 12/1999 |
| DE | 695 18 037 T2 | 3/2001 |
| EP | 0 115 812 A2 | 8/1984 |

(56) References Cited

FOREIGN PATENT DOCUMENTS

| | | |
|---|---|---|
| EP | 0 173 567 A2 | 3/1986 |
| EP | 0 115 948 B1 | 10/1986 |
| EP | 0 201 031 A2 | 11/1986 |
| EP | 0 237 233 A2 | 9/1987 |
| EP | 237233 A2 | 9/1987 |
| EP | 0 201 778 B1 | 12/1988 |
| EP | 0 184 095 B1 | 7/1989 |
| EP | 323120 | 7/1989 |
| EP | 0 201 031 B1 | 8/1989 |
| EP | 0 206 810 B1 | 4/1990 |
| EP | 0 335 645 B1 | 8/1992 |
| EP | 0 373 384 B1 | 10/1992 |
| EP | 0 537 774 A1 | 4/1993 |
| EP | 0 323 012 B1 | 5/1993 |
| EP | 0 351 076 B1 | 8/1993 |
| EP | 0 712 622 A1 | 5/1996 |
| EP | 0 509 516 B1 | 3/1997 |
| EP | 0 537 774 B1 | 1/1998 |
| EP | 0 897 710 B1 | 2/1999 |
| EP | 0 661 034 B1 | 3/1999 |
| EP | 0 712 622 B1 | 9/1999 |
| EP | 1051961 | 11/2000 |
| EP | 1051961 A1 | 11/2000 |
| EP | 1121924 A2 | 8/2001 |
| EP | 1 141 094 | 7/2002 |
| EP | 1 287 805 A1 | 3/2003 |
| EP | 1 346 717 A1 | 9/2003 |
| GB | 2 251 861 A | 7/1992 |
| JP | 59015468 | 1/1984 |
| JP | 59-135272 | 8/1984 |
| JP | 60-089752 | 5/1985 |
| JP | 61-151104 | 7/1986 |
| JP | 06-041162 | 2/1994 |
| JP | 7330530 | 12/1995 |
| JP | 10-512567 | 12/1998 |
| JP | 11139920 | 5/1999 |
| JP | 2000204010 | 7/2000 |
| JP | 2001072936 | 3/2001 |
| JP | 2004182661 | 7/2004 |
| JP | 2005-008537 | 1/2005 |
| WO | WO 98/03443 | 1/1998 |
| WO | WO 98/46198 A1 | 10/1998 |
| WO | WO 00/30591 A1 | 6/2000 |
| WO | WO 00/38619 A2 | 7/2000 |
| WO | WO 00/38619 A3 | 7/2000 |
| WO | WO 00/42092 A1 | 7/2000 |
| WO | WO 01/07444 A1 | 2/2001 |
| WO | WO 01/30304 | 5/2001 |
| WO | WO 01/30305 A1 | 5/2001 |
| WO | WO 01/30306 A1 | 5/2001 |
| WO | WO 01/30307 A1 | 5/2001 |
| WO | WO 0138449 | 5/2001 |
| WO | WO 01/92271 A1 | 12/2001 |
| WO | WO 02/02057 | 1/2002 |
| WO | WO 02/11642 | 2/2002 |
| WO | WO 02/092021 A1 | 11/2002 |
| WO | WO 03/013444 A1 | 2/2003 |
| WO | WO 03/063804 A1 | 8/2003 |
| WO | WO 03/068174 A1 | 8/2003 |
| WO | WO 2005/004819 A | 1/2005 |
| WO | WO 2005/018581 A | 3/2005 |
| WO | WO 2006/014597 | 2/2006 |
| WO | WO 2006/020760 | 2/2006 |
| WO | WO 2007-075666 | 7/2007 |

OTHER PUBLICATIONS

Buonocore et al., *J. Dent. Res.*, vol. 35, No. 6, pp. 846-851, "A Report on a Resin Composition Capable of Bonding to Human Dentin Surfaces", (1956).

Floyd Green, The Sigma-Aldrich Handbook of Stains, Dyes, & Indicators [with/Transmission Spectrum Reference], Aldrich Chem. Co., Milwaukee, WI (1990).

Holmberg et al., "Microemulsions," Chapter 6, *Surfactants and Polymers in Aqueous Solution*, Second Edition, John Wiley & Sons, pp. 138-155 (2003; Reprinted with corrections in 2004).

ISO Standard 4049:2000.

ISO Standard 7489.

ISO Standard 9917-1:2003.

Leung et al., "Ch. 9, Microemulsions: Formation, Structure, Properties, and Novel Applications," *Surfactants in Chemical/Processing Engineering*, Marcel Dekker, Inc., New York and Basel, Title page, Publication page, and pp. 315-367(1988).

Ostrovosky et al., "Mechanism of Microemulsion Formation in Systems with Low Interfacial Tension: Occurence, Properties, and Behavior of Microemulsions," *Journal of Colloid and Interface Science*, 102(1): 206-226 (Nov. 1984).

Overbeek et al., "Microemulsions," in *Surfactants*, Th. F. Thadros, Ed., Academic Press, London, Title Page, Table of Contents, pp. 111-132 (1984).

Ruckenstein et al., "Stability of Microemulsions," *J. Chem. Soc. Faraday Trans* II, vol. 71; pp. 1690-1707 (1975).

Rumphorst, et al. "Examination of the Formulation of an Innovative Single-Component Bonding System," *Signature*, vol. 6, No. 1, pp. 1-3 (Sep. 2000).

Safran et al., "Phase Diagrams for Microemulsions," *Physical Review Letters*, vol. 50, No. 24, pp. 1930-1933 (Jun. 13, 1983).

Xu et al., *J. Phys. Chem.*, 97:11350-11353 (1993).

U.S. Appl. No. 10/729,497, filed Dec. 5, 2003, entitled "Compositions Including Polymerizable Bisphosphonic Acids and Methods".

U.S. Appl. No. 60/600,658, filed Aug. 11, 2004, entitled "Self-adhesive Compositions Including a Plurality of Acidic Compounds".

Dyba et al., J. Chem. Soc., "1-Hydroxyalkane-1,1-diyldiphosphonates as potent chelating agents for metal ions. Potentiometric and spectroscopic studies of copper(II) coordination" Dalton Trans. (1996), 1119-1123.

Gumienna-Kontecka et al., J. Inorg. Biochem., Bisphosphonate chelating agents Coordination ability of 1-phenyl-1-hydroxymethylene bisphosphonate towards $Cu^{2+}$ ions, 89 (2002), 13-17.

Kieczykowski et al., J. Org. Chem., "Preparation of (4-Amino-1-Hydroxybutylidene) bisphosphonic Acid Sodium Salt, MK-217 (Alendronate Sodium). An Improved Procedure for the Preparation of 1-Hydroxy-1,1-bisphosphonic Acids," (1995), 60, 8310-8312.

Mathis et al., Dental Materials, "Properties of a New Glass Ionomer/Composite Resin Hybrid Restorative," Table of Contents, pp. 355-358.

Mathis et al., Journal of Dental Research, "Properties of a New Glass Ionomer/Composite Resin Hybrid Restorative," Abstract No. 51, vol. 66, pp. 113 (1987).

Moszner et al., Macromol. Chem. "Monomers for adhevise polymers, 2", Synthesis and radical polymerisation of hydrolytically stable acrylic phosphonic acids" Phys. 200 (1999), 1062-67.

Technical Product Profile, "3M ESPE Adper™ Prompt™ L-Pop™ and Adper™ Prompt™ Self-Etch adhesives," Title page, Table of Contents, and pp. 3, 5-23, and Publication Page, 3M IPC (2002).

Tromelin et al., "Cetophosphonates et Esters Cycliques D'Hydroxymethylenes Diphosphonates Syntheses, Structures et Hydrolyse," Phosphorus Sufur Relat. Elem. 27, (1986), pp. 301-312.

Palma, R.G.; Turbino, M.L.; Watson, E.; Powers, J.M.: "Bond Strength to dentin with artificial carious lesions: influence of caries detecting dye" American Journal of Dentistry, vol. 11, No. 3, 1998, pp. 128-130, XP008055059 abstract.

Kazemi, R.B.; Meiers, J.C.; Peppers, K: "Effect of caries desclosing agents on bond strengths of total-etch and self-etching primer dentin bonding systems to resin composite" Operative Dentistry, vol. 27, No. 3, 2002, pp. 238-242, XP008054961, whole document.

TYRIAN™SPE Universal Self-Priming Etchant, TYRIAN SPE General Information, BISCO, Inc., Schaumburg, IL [retrieved from the internet on Jul. 7, 2004] URL http://www.bisco.com/instructions/tyrianspe_instr_print.asp 8 pages.

S. J. Hodges et al., Unusual Indelible Enamel Staining Following Fixed Appliance Treatment, 2000, pp. 303-306, vol. 27, copyright 2000 British Orthodontic Society.

Written Opinion of ISR for PCT/US2005/02491.

Written Opinion of ISR for PCT/US2004/025936.

(56) References Cited

OTHER PUBLICATIONS

IPER for PCT/US03/41487, Apr. 12, 2005.
Alberti, "Cationic Dyes for Acrylic Fibers IV. Catonic Dyes from 6-Methyl-2-(p-Aminophenyl) Benzothiazole and Angular 2-Aminonapthtothiazoles", Chimica e L'Industria, 1974, vol. 56, No. 10, pp. 684-686.
Billmeyer, Principles of Color Technology, Second Edition, New York, NY (1981).
"Blue No. 403", [online], [retrieved from the internet on Aug. 24, 2006], <http://www02.so-net.ne.jp/~tombo/ci/b403e.htm>, 1 page.
Clinpro Sealant, Technical Product Profile, No. 70-2009-2265-9, 3M ESPE, (2001), pp. 1-20.
"Color Center, Color Handbook, Anthrapyrimidine", Special Chem Innovations and Solutions [on line], [retrieved from the internet on Aug. 24, 2006], <http://www.specialchem4coatings.com/tc/color-handbook>, 2 pages.
"Colour Index", The Society of Dyers and Colourists [on line], [retrieved from the internet on Nov. 29, 2005], <http://www.sdc.org.uk/publications/ci4classes.htm>, 2 pages.
"Disperse Dyes", Technology Information Forecasting and Assessment Council, Asian and Pacific Centre for Transfer of Technology, [on line], [retrieved from the internet on Nov. 28, 2005], <http://www.tifac.org.in/offer/tsw/apctt10.htm>, 4 pages.
"Dye Classes for Principal Applications," Dr. Klaus Hunger (author and editor), Wiley Interscience Online Book, [retrieved from the internet on Nov. 29, 2005], <http://www.3.interscience.wiley.com/cgi-bin/summary/107642439/SUMMARY>, 3 pages.
"Epochem Products 2004", Epochem Co., Ltd, <http://www.Epochem.com>, 2002-2004, pp. 1-25.
"Essay: Dyes and Dyeing", Supplement to Experiment 9, Univ. of CO, Boulder, Dept. of Chem. and Biochem. 2006, pp. 63-70.
Freeman, "Synthetic Dyes Based on Toxicological Considerations", National Textile Center Annual Report, Sep. 1993, pp. 167-176.
Green, The Sigma-Aldrich Handbook of Stains, Dyes, and Indicators, Aldrich Chemical Company, pp. 284, 290, 291, 398, 647, 660, (1990).
Heitzman, "Organic Yellows for Plastics", Sun Chemical Corporation, Performance Plastics Business Unit, pp. 12-15.
"ONE-UP Bond F" literature, Tokuyama Corp., Product description and general information, 1 page, [date unknown but believed to be prior to the date of the filing of the present application].
Patel, "Synthesis of Monoazo Disperse Dyes from 2-Amino-4-Methylbenzothiazole and Their Application on Polyester Fiber", Oriental Journal Chemistry, 1996, vol. 12, No. 2, pp. 193-195.
StainsFile, "Anthraquinone Dyes", [retrieved from the internet on Nov. 28, 2005], <http://stasfile.info.StainsFile/dyes/class/clsanthq.htm>, 1 page.
The Complete Technology Book on Dyes & Dye Intermediates, National Institute of Industrial Research [on line], [retrieved from the internet on Nov. 29, 2005], <http://www.niir.org>, pp. 1-42. [ISBN: 81-86623-79-5].
Twenty-first Report of the Interagency Testing Committee to the Administrator; Receipt of Report and Request for Comments Regarding Priority List of Chemicals, Notices, Federal Register, vol. 52, No. 224, Nov. 1987, pp. 44830-44837.
International Search Report for Int'l Appln. No. PCT/US2003/041487, 3 pages, Jun. 9, 2004.
International Search Report for Int'l Appln. No. PCT/US2004/025936, 3 pages, Dec. 15, 2004.
International Search Report for Int'l Appln. No. PCT/US2005/024291, 4 pages, Nov. 21, 2005.
International Search Report for Int'l Appln. No. PCT/US2005/028536, 4 pages, Dec. 6, 2005.
International Search Report for Int'l Appln. No. PCT/US2007/087192, 3 pages, Jan. 19, 2009.
International Preliminary Report on Patentability and Written Opinion for PCT/US2005/028536; 7 pgs, Feb. 13, 2007.

* cited by examiner

SELF-ADHESIVE COMPOSITIONS INCLUDING A PLURALITY OF ACIDIC COMPOUNDS

CROSS REFERENCE TO RELATED APPLICATIONS

This application is a national stage filing under 35 U.S.C. 371 of PCT/US2005/028536 filed Aug. 9, 2005, which claims priority to provisional application 60/600,658, filed Aug. 11, 2004, the disclosure of each of which is incorporated by reference in their entirety herein.

BACKGROUND

Self-adhesive compositions that can bond to an untreated dental structure (i.e., a structure not pre-treated with an etchant, primer, or bonding agent) are known in the art. Such compositions are useful, for example, in dental and orthodontic procedures involving restorative compositions (e.g., filling materials and orthodontic adhesives). Preferably, such self-adhesive compositions are one-part, shelf-stable compositions.

Conventional restorative compositions, while capable of exhibiting excellent mechanical properties (e.g., flexural modulus and compressive strength), require a separate etching and/or bonding step to provide adequate adhesion to a dental structure. Self-adhesive compositions, which are also self-etching, are known to result in good adhesion to both untreated and treated dental structure. However, self-adhesive compositions that exhibit good adhesion to untreated dental structure often lack the excellent mechanical properties of conventional restoratives.

There is a need for self-adhesive compositions having excellent mechanical properties and good adhesion to untreated dental structures.

SUMMARY OF THE INVENTION

In one aspect, the present invention provides a self-adhesive composition. In some embodiments, the self-adhesive composition is for use as a restorative for a dental structure. In some embodiments, the self-adhesive composition is for use in adhering an orthodontic appliance to a tooth surface.

The self-adhesive composition includes: a first compound including at least one (meth)acryloxy group and at least one —O—P(O)(OH)$_x$ group, wherein x=1 or 2, and wherein the at least one —O—P(O)(OH)$_x$ group and the at least one (meth)acryloxy group are linked together by a C1-C4 hydrocarbon group; a second compound including at least one (meth)acryloxy group and at least one —O—P(O)(OH)$_x$ group, wherein x=1 or 2, and wherein the at least one —O—P(O)(OH)$_x$ group and the at least one (meth)acryloxy group are linked together by a C5-C12 hydrocarbon group; an ethylenically unsaturated compound without acid functionality; an initiator system; and a filler wherein the self-adhesive composition includes at least 40% by weight filler. Preferably the composition is non-aqueous.

In another aspect, the present invention provides a method of restoring a dental structure. The method includes: applying a self-adhesive composition as described herein to a dental structure surface; and hardening the self-adhesive composition under conditions effective to form a bond between the hardened composition and the dental structure. Typically, the dental structure surface includes enamel, dentin, or cementum. Oftentimes, the dental structure surface is unetched prior to applying the self-adhesive composition. For embodiments in which the self-adhesive composition is non-aqueous, the dental structure surface is preferably wet prior to applying the self-adhesive composition. For example, an aqueous diluent can be applied to an unetched dental structure surface to provide a wet, unetched dental structure surface.

In another aspect, the present invention provides a method of adhering an orthodontic appliance to a tooth.

In one embodiment, the method includes: applying a self-adhesive composition as described herein to a tooth surface under conditions effective to cause the self-adhesive composition to etch the tooth surface; applying an orthodontic appliance to the tooth surface having the self-adhesive composition applied thereon; and hardening the self-adhesive composition under conditions effective to form a bond between the orthodontic appliance and the tooth.

In another embodiment, the method includes: applying an orthodontic appliance having thereon, a self-adhesive composition as described herein, to a wet tooth surface under conditions effective to cause the self-adhesive composition to etch the tooth surface; and hardening the self-adhesive composition under conditions effective to form a bond between the orthodontic appliance and the tooth. In some embodiments, the self-adhesive composition can be applied to an orthodontic appliance to provide the orthodontic appliance having the self-adhesive composition thereon. Alternatively, the orthodontic appliance having the self-adhesive composition thereon can be provided as a precoated orthodontic appliance.

DEFINITIONS

As used herein, "adhesive" or "dental adhesive" refers to a composition used as a pre-treatment on a dental structure (e.g., a tooth) to adhere a "dental material" (e.g., "restorative," an orthodontic appliance (e.g., bracket), or an "orthodontic adhesive") to the dental structure. An "orthodontic adhesive" refers to a highly (generally greater than 40% by weight) filled composition (more analogous to a "restorative material" than to a "dental adhesive") used to adhere an orthodontic appliance to a dental structure (e.g., tooth) surface. Generally, the dental structure surface is pre-treated, e.g., by etching, priming, and/or applying an adhesive to enhance the adhesion of the "orthodontic adhesive" to the dental structure surface.

As used herein, a "non-aqueous" composition (e.g., an adhesive) refers to a composition in which water has not been added as a component. However, there may be adventitious water in other components of the composition, but the total amount of water does not adversely affect stability (e.g., the shelf-life) of the non-aqueous composition. Non-aqueous compositions preferably include less than 1% by weight, more preferably less than 0.5% by weight, and most preferably less than 0.1% by weight water, based on the total weight of the non-aqueous composition.

As used herein, a "self-etching" composition refers to a composition that bonds to a dental structure surface without pretreating the dental structure surface with an etchant. Preferably, a self-etching composition can also function as a self-primer wherein no separate etchant or primer are used.

As used herein, a "self-adhesive" composition refers to a composition that is capable of bonding to a dental structure surface without pretreating the dental structure surface with a primer or bonding agent. Preferably, a self-adhesive composition is also a self-etching composition wherein no separate etchant is used.

As used herein, a "(meth)acryloxy" group is a shorthand term referring to either an acryloxy group (i.e., CH$_2$=CHC(O)O—) and/or a methacryloxy group (i.e., CH$_2$=C(CH$_3$)C(O)O—).

As used herein, a "hydrocarbon" group is an organic group consisting of the elements carbon and hydrogen.

As used herein, a "hydrophilic" compound refers to a compound having the ability to wet a dental structure surface sufficient to enable a self-adhesive composition containing the compound to form an effective bond between the hardened composition and the dental structure.

As used herein, a "hydrophobic" compound refers to a compound not having the ability to wet a dental structure surface sufficient to enable a self-adhesive composition containing the compound to form an effective bond between the hardened composition and the dental structure. However, a "hydrophobic" compound can be effective in providing hardened compositions having high flexural and compressive strength values.

As used herein, "hardening" or "curing" a composition are used interchangeably and refer to polymerization and/or crosslinking reactions including, for example, photopolymerization reactions and chemical polymerization techniques (e.g., ionic reactions reactions or chemical reactions forming radicals effective to polymerize ethylenically unsaturated compounds) involving one or more materials included in the composition.

As used herein, a "dental structure surface" refers to tooth structures (e.g., enamel, dentin, and cementum) and bone.

As used herein, an "uncut" dental structure surface refers to a dental structure surface that has not been prepared by cutting, grinding, drilling, etc.

As used herein, an "untreated" dental structure surface refers to a tooth or bone surface that has not been treated with an etchant, primer, or bonding agent prior to application of a self-etching adhesive or a self-adhesive composition of the present invention.

As used herein, an "unetched" dental structure surface refers to a tooth or bone surface that has not been treated with an etchant prior to application of a self-etching adhesive or a self-adhesive composition of the present invention.

As used herein, an "etchant" refers to an acidic composition that is capable of fully or partially solubilizing (i.e., etching) a dental structure surface. The etching effect can be visible to the naked human eye and/or instrumentally detectably (e.g., by light microscopy). Typically, an etchant is applied to the dental structure surface for a period of about 10 to 30 seconds.

As used herein, a "wet" dental structure surface refers to a surface of a dental structure upon which an aqueous liquid (e.g., water or saliva) is present and visible to the naked human eye.

As used herein, a "dry" dental structure surface refers to a surface of a dental structure that has been dried (e.g., air dried) and does not have present visible water.

As used herein, "dental material" refers to a material that may be bonded to a dental structure surface and includes, for example, dental restoratives, orthodontic appliances, and/or orthodontic adhesives.

As used herein, "a" or "an" means "at least one" or "one or more" unless otherwise indicated.

DETAILED DESCRIPTION OF ILLUSTRATIVE EMBODIMENTS

Self-adhesive compositions of the present invention are useful for treating hard surfaces, preferably, hard tissues such as dentin, enamel, and bone. Compositions of the present invention can be used as a restorative material (e.g., filling material) without the need for an etchant, primer, or adhesive.

Self-adhesive compositions are typically prepared by combining polymerizable components (e.g., ethylenically unsaturated compounds with acid functionality and ethylenically unsaturated compounds without acid functionality), a filler, and an initiator system. Exemplary self-adhesive compositions are disclosed, for example, in U.S. patent application Ser. No. 10/916,240, filed Aug. 11, 2004. Typically, the selection of polymerizable components is made to impart the desired etching, priming, adhesive, and/or restorative properties to the compositions. Generally, techniques for selecting polymerizable components and optional other components to impart etching, priming, adhesive, and/or restorative properties to hard-surface treatment compositions are well known to those skilled in formulation of dental materials. Suitable polymerizable components for use in such compositions, dental adhesives, and dental restoratives are discussed herein.

Self-adhesive compositions of the present invention include two or more ethylenically unsaturated compounds with acid functionality, one or more ethylenically unsaturated compounds without acid functionality, an initiator system, and a filler.

The two or more ethylenically unsaturated compounds with acid functionality each include at least one (meth)acryloxy group and at least one —O—P(O)(OH)$_x$ group, wherein x=1 or 2.

In one of the ethylenically unsaturated compounds with acid functionality, the at least one —O—P(O)(OH)$_x$ group and the at least one (meth)acryloxy group are linked together by a C1-C4 hydrocarbon group, preferably a C1-C3 hydrocarbon group, and more preferably a C2 hydrocarbon group. Such ethylenically unsaturated compounds include, for example, compounds of Formula I

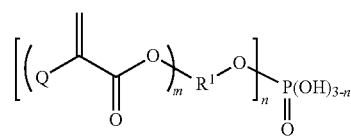

wherein m and n are each independently 1 or 2, Q is hydrogen or a methyl group, and R$^1$ is a C1-C4 hydrocarbon group, preferably a C1-C3 hydrocarbon group, and more preferably a C2 hydrocarbon group. Such ethylenically unsaturated compounds with acid functionality are typically hydrophilic.

Suitable compounds of Formula I, which are typically hydrophilic compounds, include, for example, hydroxyethyl (meth)acrylate (e.g., HEMA) phosphates, bis((meth)acryloxyethyl) phosphate, ((meth)acryloxypropyl) phosphate, bis ((meth)acryloxypropyl) phosphate, bis((meth)acryloxy)propyloxy phosphate, and combinations thereof.

In another of the ethylenically unsaturated compounds with acid functionality, the at least one —O—P(O)(OH)$_x$ group and the at least one (meth)acryloxy group are linked together by a C5-C12 hydrocarbon group, preferably a C6-C10, and more preferably a C6 hydrocarbon group. Such ethylenically unsaturated compounds include, for example, compounds of Formula II

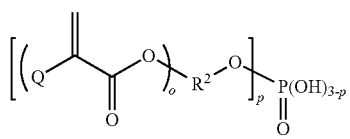

wherein o and p are each independently 1 or 2, Q is hydrogen or a methyl group, and $R^2$ is a C5-C12 hydrocarbon group, preferably a C6-C10, and more preferably a C6 hydrocarbon group. Such ethylenically unsaturated compounds with acid functionality are typically hydrophobic.

Suitable compounds of Formula II, which are typically hydrophobic compounds, include, for example, (meth)acryloxyhexyl phosphate, bis((meth)acryloxyhexyl) phosphate, (meth)acryloxyoctyl phosphate, bis((meth)acryloxyoctyl) phosphate, (meth)acryloxydecyl phosphate, bis((meth)acryloxydecyl) phosphate, and combinations thereof.

Typically, one of skill in the art may select hydrophilic ethylenically unsaturated compound(s) for use in a self-adhesive restorative composition to provide good adhesion. However, the resulting composition oftentimes has poor mechanical properties. Conversely, one of skill in the art may select hydrophobic ethylenically unsaturated compound(s) for use in a self-adhesive restorative composition to provide good mechanical properties. However, the resulting composition oftentimes exhibits little or no adhesion. The present invention discloses combinations of hydrophilic and hydrophobic ethylenically unsaturated compounds that can lead to self-adhesive compositions having both good adhesion and good mechanical properties.

Compounds of Formula I (i.e., typically hydrophilic compounds) and Formula II (i.e., typically hydrophobic compounds) are preferably used in a weight/weight ratio of at least 1:5 (Formula I to Formula II), and more preferably at least 1:4 (Formula I to Formula II). Compounds of Formula I (i.e., typically hydrophilic compounds) and Formula II (i.e., typically hydrophobic compounds) are preferably used in a weight/weight ratio of at most 10:1 (Formula I to Formula II), and more preferably at most 4:1 (Formula I to Formula II).

In addition to the two or more ethylenically unsaturated compounds with acid functionality discussed herein above, self-adhesive compositions of the present invention can include additional ethylenically unsaturated compounds with acid functionality as desired. As used herein, ethylenically unsaturated compounds with acid functionality is meant to include monomers, oligomers, and polymers having ethylenic unsaturation and acid and/or acid-precursor functionality. Acid-precursor functionalities include, for example, anhydrides, acid halides, and pyrophosphates.

Ethylenically unsaturated compounds with acid functionality include, for example, α,β-unsaturated acidic compounds such as glycerol phosphate monomethacrylates, glycerol phosphate dimethacrylates, caprolactone methacrylate phosphate, citric acid di- or tri-methacrylates, poly(meth)acrylated oligomaleic acid, poly(meth)acrylated polymaleic acid, poly(meth)acrylated poly(meth)acrylic acid, poly(meth)acrylated polycarboxyl-polyphosphonic acid, poly(meth)acrylated polychlorophosphoric acid, poly(meth)acrylated polysulfonate, poly(meth)acrylated polyboric acid, and the like, may be used as components in the hardenable resin system. Also monomers, oligomers, and polymers of unsaturated carbonic acids such as (meth)acrylic acids, aromatic (meth)acrylated acids (e.g., methacrylated trimellitic acids), and anhydrides thereof can be used. Certain preferred compositions of the present invention include an ethylenically unsaturated compound with acid functionality having at least one P—OH moiety.

Certain of these compounds are obtained, for example, as reaction products between isocyanatoalkyl (meth)acrylates and carboxylic acids. Additional compounds of this type having both acid-functional and ethylenically unsaturated components are described in U.S. Pat. No. 4,872,936 (Engelbrecht) and U.S. Pat. No. 5,130,347 (Mitra). A wide variety of such compounds containing both the ethylenically unsaturated and acid moieties can be used. Mixtures of such compounds can be used if desired.

Additional ethylenically unsaturated compounds with acid functionality include, for example, polymerizable bisphosphonic acids as disclosed for example, in U.S. Patent Application Publication No. 2004/0206932 (Abuelyaman); AA:ITA:IEM (copolymer of acrylic acid:itaconic acid with pendent methacrylate made by reacting AA:ITA copolymer with sufficient 2-isocyanatoethyl methacrylate to convert a portion of the acid groups of the copolymer to pendent methacrylate groups as described, for example, in Example 11 of U.S. Pat. No. 5,130,347 (Mitra)); and those recited in U.S. Pat. No. 4,259,075 (Yamauchi et al.), U.S. Pat. No. 4,499,251 (Omura et al.), U.S. Pat. No. 4,537,940 (Omura et al.), U.S. Pat. No. 4,539,382 (Omura et al.), U.S. Pat. No. 5,530,038 (Yamamoto et al.), U.S. Pat. No. 6,458,868 (Okada et al.), and European Pat. Application Publication Nos. EP 712,622 (Tokuyama Corp.) and EP 1,051,961 (Kuraray Co., Ltd.).

Preferably, the compositions of the present invention include at least 1% by weight, more preferably at least 3% by weight, and most preferably at least 5% by weight ethylenically unsaturated compounds with acid functionality, based on the total weight of the unfilled composition. Preferably, compositions of the present invention include at most 80% by weight, more preferably at most 70% by weight, and most preferably at most 60% by weight ethylenically unsaturated compounds with acid functionality, based on the total weight of the unfilled composition.

Ethylenically Unsaturated Compounds without Acid Functionality

The compositions of the present invention also include one or more polymerizable components in addition to the ethylenically unsaturated compounds with acid functionality, thereby forming hardenable compositions. The polymerizable components may be monomers, oligomers, or polymers. In some embodiments, the ethylenically unsaturated compound without acid functionality includes at least two ethylenically unsaturated groups (e.g., acryloxy groups, methacryloxy groups, vinyl groups, styryl groups, and combinations thereof) per molecule (e.g., at least two methacryloxy groups per molecule).

In certain embodiments, the compositions are photopolymerizable, i.e., the compositions contain a photopolymerizable component and a photoinitiator (i.e., a photoinitiator system) that upon irradiation with actinic radiation initiates the polymerization (or hardening) of the composition. Such photopolymerizable compositions can be free radically polymerizable.

In certain embodiments, the compositions are chemically polymerizable, i.e., the compositions contain a chemically polymerizable component and a chemical initiator (i.e., initiator system) that can polymerize, cure, or otherwise harden the composition without dependence on irradiation with actinic radiation. Such chemically polymerizable compositions are sometimes referred to as "self-cure" compositions and may include glass ionomer cements, resin-modified glass ionomer cements, redox cure systems, and combinations thereof.

Preferably, compositions of the present invention include at least 5% by weight, more preferably at least 10% by weight, and most preferably at least 15% by weight ethylenically unsaturated compounds without acid functionality, based on the total weight of the unfilled composition. Preferably, compositions of the present invention include at most 95% by weight, more preferably at most 90% by weight, and most preferably at most 80% by weight ethylenically unsaturated compounds without acid functionality, based on the total weight of the unfilled composition.

Photopolymerizable Compositions

Suitable photopolymerizable compositions may include photopolymerizable components (e.g., compounds) that include ethylenically unsaturated compounds (which contain free radicals active unsaturated groups). Examples of useful ethylenically unsaturated compounds include acrylic acid esters, methacrylic acid esters, hydroxy-functional acrylic acid esters, hydroxy-functional methacrylic acid esters, and combinations thereof.

Photopolymerizable compositions may include compounds having free radically active functional groups that may include monomers, oligomers, and polymers having one or more ethylenically unsaturated group. Suitable compounds contain at least one ethylenically unsaturated bond and are capable of undergoing addition polymerization. Such free radically polymerizable compounds include mono-, di- or poly-(meth)acrylates (i.e., acrylates and methacrylates) such as, methyl (meth)acrylate, ethyl acrylate, isopropyl methacrylate, n-hexyl acrylate, stearyl acrylate, allyl acrylate, glycerol triacrylate, ethyleneglycol diacrylate, diethyleneglycol diacrylate, triethyleneglycol dimethacrylate, 1,3-propanediol di(meth)acrylate, trimethylolpropane triacrylate, 1,2,4-butanetriol trimethacrylate, 1,4-cyclohexanediol diacrylate, pentaerythritol tetra(meth)acrylate, sorbitol hexacrylate, tetrahydrofurfuryl (meth)acrylate, bis[1-(2-acryloxy)]-p-ethoxyphenyldimethylmethane, bis[1-(3-acryloxy-2-hydroxy)]-p-propoxyphenyldimethylmethane, ethoxylated bisphenolA di(meth)acrylate, and trishydroxyethyl-isocyanurate trimethacrylate; (meth)acrylamides (i.e., acrylamides and methacrylamides) such as (meth)acrylamide, methylene bis-(meth)acrylamide, and diacetone (meth) acrylamide; urethane (meth)acrylates; the bis-(meth)acrylates of polyethylene glycols (preferably of molecular weight 200-500), copolymerizable mixtures of acrylated monomers such as those in U.S. Pat. No. 4,652,274 (Boettcher et al.), acrylated oligomers such as those of U.S. Pat. No. 4,642,126 (Zador et al.), and poly(ethylenically unsaturated) carbamoyl isocyanurates such as those disclosed in U.S. Pat. No. 4,648,843 (Mitra); and vinyl compounds such as styrene, diallyl phthalate, divinyl succinate, divinyl adipate and divinyl phthalate. Other suitable free radically polymerizable compounds include siloxane-functional (meth)acrylates as disclosed, for example, in WO-00/38619 (Guggenberger et al.), WO-01/92271 (Weinmann et al.), WO-01/07444 (Guggenberger et al.), WO-00/42092 (Guggenberger et al.) and fluoropolymer-functional (meth)acrylates as disclosed, for example, in U.S. Pat. No. 5,076,844 (Fock et al.), U.S. Pat. No. 4,356,296 (Griffith et al.), EP-0373 384 (Wagenknecht et al.), EP-0201 031 (Reiners et al.), and EP-0201 778 (Reiners et al.). Mixtures of two or more free radically polymerizable compounds can be used if desired.

The polymerizable component may also contain hydroxyl groups and free radically active functional groups in a single molecule. Examples of such materials include hydroxyalkyl (meth)acrylates, such as 2-hydroxyethyl (meth)acrylate and 2-hydroxypropyl (meth)acrylate; glycerol mono- or di-(meth)acrylate; trimethylolpropane mono- or di-(meth)acrylate; pentaerythritol mono-, di-, and tri-(meth)acrylate; sorbitol mono-, di-, tri-, tetra-, or penta-(meth)acrylate; and 2,2-bis[4-(2-hydroxy-3-methacryloxypropoxy)phenyl]propane (bisGMA). Suitable ethylenically unsaturated compounds are also available from a wide variety of commercial sources, such as Sigma-Aldrich, St. Louis. Mixtures of ethylenically unsaturated compounds can be used if desired.

Preferred photopolymerizable components include PEGDMA (polyethyleneglycol dimethacrylate having a molecular weight of approximately 400), bisGMA, UDMA (urethane dimethacrylate), GDMA (glycerol dimethacrylate), TEGDMA (triethyleneglycol dimethacrylate), bisEMA6 as described in U.S. Pat. No. 6,030,606 (Holmes), and NPGDMA (neopentylglycol dimethacrylate). Various combinations of the polymerizable components can be used if desired.

Suitable photoinitiators (i.e., photoinitiator systems that include one or more compounds) for polymerizing free radically photopolymerizable compositions include binary and tertiary systems. Typical tertiary photoinitiators include an iodonium salt, a photosensitizer, and an electron donor compound as described in U.S. Pat. No. 5,545,676 (Palazzotto et al.). Preferred iodonium salts are the diaryl iodonium salts, e.g., diphenyliodonium chloride, diphenyliodonium hexafluorophosphate, diphenyliodonium tetrafluoroborate, and tolylcumyliodonium tetrakis(pentafluorophenyl)borate. Preferred photosensitizers are monoketones and diketones that absorb some light within a range of 400 nm to 520 nm (preferably, 450 nm to 500 nm). More preferred compounds are alpha diketones that have some light absorption within a range of 400 nm to 520 nm (even more preferably, 450 to 500 nm). Preferred compounds are camphorquinone, benzil, furil, 3,3,6,6-tetramethylcyclohexanedione, phenanthraquinone, 1-phenyl-1,2-propanedione and other 1-aryl-2-alkyl-1,2-ethanediones, and cyclic alpha diketones. Most preferred is camphorquinone. Preferred electron donor compounds include substituted amines, e.g., ethyl dimethylaminobenzoate. Other suitable tertiary photoinitiator systems useful for photopolymerizing cationically polymerizable resins are described, for example, in U.S. Pat. No. 6,765,036 (Dede et al.).

Other suitable photoinitiators for polymerizing free radically photopolymerizable compositions include the class of phosphine oxides that typically have a functional wavelength range of 380 nm to 1200 nm. Preferred phosphine oxide free radical initiators with a functional wavelength range of 380 nm to 450 nm are acyl and bisacyl phosphine oxides such as those described in U.S. Pat. No. 4,298,738 (Lechtken et al.), U.S. Pat. No. 4,324,744 (Lechtken et al.), U.S. Pat. No. 4,385,109 (Lechtken et al.), U.S. Pat. No. 4,710,523 (Lechtken et al.), and U.S. Pat. No. 4,737,593 (Ellrich et al.), U.S. Pat. No. 6,251,963 (Kohler et al.); and EP Application No. 0 173 567 A2 (Ying).

Commercially available phosphine oxide photoinitiators capable of free-radical initiation when irradiated at wavelength ranges of greater than 380 nm to 450 nm include bis(2,4,6-trimethylbenzoyl)phenyl phosphine oxide (IRGACURE 819, Ciba Specialty Chemicals, Tarrytown, N.Y.), bis (2,6-dimethoxybenzoyl)-(2,4,4-trimethylpentyl) phosphine oxide (CGI 403, Ciba Specialty Chemicals), a 25:75 mixture, by weight, of bis(2,6-dimethoxybenzoyl)-2,4,4-trimethylpentyl phosphine oxide and 2-hydroxy-2-methyl-1-phenyl-propan-1-one (IRGACURE 1700, Ciba Specialty Chemicals), a 1:1 mixture, by weight, of bis(2,4,6- trimethylbenzoyl)phenyl phosphine oxide and 2-hydroxy-2-methyl-1-phenylpropane-1-one (DAROCUR 4265, Ciba Specialty Chemicals), and ethyl 2,4,6-trimethylbenzylphenyl phosphinate (LUCIRIN LR8893X, BASF Corp., Charlotte, N.C.).

Typically, the phosphine oxide initiator is present in the photopolymerizable composition in catalytically effective amounts, such as from 0.1 weight percent to 5.0 weight percent, based on the total weight of the composition.

Tertiary amine reducing agents may be used in combination with an acylphosphine oxide. Illustrative tertiary amines useful in the invention include ethyl 4-(N,N-dimethylamino) benzoate and N,N-dimethylaminoethyl methacrylate. When present, the amine reducing agent is present in the photopolymerizable composition in an amount from 0.1 weight percent to 5.0 weight percent, based on the total weight of the composition. Useful amounts of other initiators are well known to those of skill in the art.

Chemically Polymerizable Compositions

The chemically polymerizable compositions may include redox cure systems that include a polymerizable component (e.g., an ethylenically unsaturated polymerizable component) and redox agents that include an oxidizing agent and a reducing agent. Suitable polymerizable components, redox agents, optional acid-functional components, and optional fillers that are useful in the present invention are described in U.S. Pat. Publication Nos. 2003/0166740 (Mitra et al.) and 2003/0195273 (Mitra et al.).

The reducing and oxidizing agents should react with or otherwise cooperate with one another to produce free-radicals capable of initiating polymerization of the resin system (e.g., the ethylenically unsaturated component). This type of cure is a dark reaction, that is, it is not dependent on the presence of light and can proceed in the absence of light. The reducing and oxidizing agents are preferably sufficiently shelf-stable and free of undesirable colorization to permit their storage and use under typical dental conditions. They should be sufficiently miscible with the resin system (and preferably water-soluble) to permit ready dissolution in (and discourage separation from) the other components of the polymerizable composition.

Useful reducing agents include ascorbic acid, ascorbic acid derivatives, and metal complexed ascorbic acid compounds as described in U.S. Pat. No. 5,501,727 (Wang et al.); amines, especially tertiary amines, such as 4-tert-butyl dimethylaniline; aromatic sulfinic salts, such as p-toluenesulfinic salts and benzenesulfinic salts; thioureas, such as 1-ethyl-2-thiourea, tetraethyl thiourea, tetramethyl thiourea, 1,1-dibutyl thiourea, and 1,3-dibutyl thiourea; and mixtures thereof. Other secondary reducing agents may include cobalt (II) chloride, ferrous chloride, ferrous sulfate, hydrazine, hydroxylamine (depending on the choice of oxidizing agent), salts of a dithionite or sulfite anion, and mixtures thereof. Preferably, the reducing agent is an amine.

Suitable oxidizing agents will also be familiar to those skilled in the art, and include but are not limited to persulfuric acid and salts thereof, such as sodium, potassium, ammonium, cesium, and alkyl ammonium salts. Additional oxidizing agents include peroxides such as benzoyl peroxides, hydroperoxides such as cumyl hydroperoxide, t-butyl hydroperoxide, and amyl hydroperoxide, as well as salts of transition metals such as cobalt (III) chloride and ferric chloride, cerium (IV) sulfate, perboric acid and salts thereof, permanganic acid and salts thereof, perphosphoric acid and salts thereof, and mixtures thereof.

It may be desirable to use more than one oxidizing agent or more than one reducing agent. Small quantities of transition metal compounds may also be added to accelerate the rate of redox cure. In some embodiments it may be preferred to include a secondary ionic salt to enhance the stability of the polymerizable composition as described in U.S. Pat. Publication No. 2003/0195273 (Mitra et al.).

The reducing and oxidizing agents are present in amounts sufficient to permit an adequate free-radical reaction rate. This can be evaluated by combining all of the ingredients of the polymerizable composition except for the optional filler, and observing whether or not a hardened mass is obtained.

Preferably, the reducing agent is present in an amount of at least 0.01% by weight, and more preferably at least 0.1% by weight, based on the total weight (including water) of the components of the polymerizable composition. Preferably, the reducing agent is present in an amount of no greater than 10% by weight, and more preferably no greater than 5% by weight, based on the total weight (including water) of the components of the polymerizable composition.

Preferably, the oxidizing agent is present in an amount of at least 0.01% by weight, and more preferably at least 0.10% by weight, based on the total weight (including water) of the components of the polymerizable composition. Preferably, the oxidizing agent is present in an amount of no greater than 10% by weight, and more preferably no greater than 5% by weight, based on the total weight (including water) of the components of the polymerizable composition.

The reducing or oxidizing agents can be microencapsulated as described in U.S. Pat. No. 5,154,762 (Mitra et al.). This will generally enhance shelf stability of the polymerizable composition, and if necessary permit packaging the reducing and oxidizing agents together. For example, through appropriate selection of an encapsulant, the oxidizing and reducing agents can be combined with an acid-functional component and optional filler and kept in a storage-stable state. Likewise, through appropriate selection of a water-insoluble encapsulant, the reducing and oxidizing agents can be combined with an FAS glass and water and maintained in a storage-stable state.

A redox cure system can be combined with other cure systems, e.g., with a photopolymerizable composition such as described U.S. Pat. No. 5,154,762 (Mitra et al.).

Fillers

The compositions of the present invention can also contain fillers. Fillers may be selected from one or more of a wide variety of materials suitable for incorporation in compositions used for dental applications, such as fillers currently used in dental restorative compositions, and the like.

The filler is preferably finely divided. The filler can have a unimodial or polymodial (e.g., bimodal) particle size distribution. Preferably, the maximum particle size (the largest dimension of a particle, typically, the diameter) of the filler is less than 20 micrometers, more preferably less than 10 micrometers, and most preferably less than 5 micrometers. Preferably, the average particle size of the filler is less than 0.1 micrometers, and more preferably less than 0.075 micrometer.

The filler can be an inorganic material. It can also be a crosslinked organic material that is insoluble in the resin system, and is optionally filled with inorganic filler. The filler should in any event be nontoxic and suitable for use in the mouth. The filler can be radiopaque or radiolucent. The filler typically is substantially insoluble in water.

Examples of suitable inorganic fillers are naturally occurring or synthetic materials including, but not limited to: quartz; nitrides (e.g., silicon nitride); glasses derived from, for example, Zr, Sr, Ce, Sb, Sn, Ba, Zn, and Al; feldspar; borosilicate glass; kaolin; talc; titania; low Mohs hardness fillers such as those described in U.S. Pat. No. 4,695,251 (Randklev); and submicron silica particles (e.g., pyrogenic silicas such as those available under the trade designations AEROSIL, including "OX 50," "130," "150" and "200" silicas from Degussa Corp., Akron, Ohio and CAB-O-SIL M5 silica from Cabot Corp., Tuscola, Ill.). Examples of suitable organic filler particles include filled or unfilled pulverized polycarbonates, polyepoxides, and the like.

Preferred non-acid-reactive filler particles are quartz, submicron silica, and non-vitreous microparticles of the type described in U.S. Pat. No. 4,503,169 (Randklev). Mixtures of these non-acid-reactive fillers are also contemplated, as well as combination fillers made from organic and inorganic materials. Silane-treated zirconia-silica (Zr—Si) filler is especially preferred in certain embodiments.

The filler can also be an acid-reactive filler. Suitable acid-reactive fillers include metal oxides, glasses, and metal salts. Typical metal oxides include barium oxide, calcium oxide, magnesium oxide, and zinc oxide. Typical glasses include borate glasses, phosphate glasses, and fluoroaluminosilicate ("FAS") glasses. FAS glasses are particularly preferred. The FAS glass typically contains sufficient elutable cations so that a hardened dental composition will form when the glass is mixed with the components of the hardenable composition. The glass also typically contains sufficient elutable fluoride ions so that the hardened composition will have cariostatic properties. The glass can be made from a melt containing fluoride, alumina, and other glass-forming ingredients using techniques familiar to those skilled in the FAS glassmaking art. The FAS glass typically is in the form of particles that are sufficiently finely divided so that they can conveniently be mixed with the other cement components and will perform well when the resulting mixture is used in the mouth.

Generally, the average particle size (typically, diameter) for the FAS glass is no greater than about 12 micrometers, typically no greater than 10 micrometers, and more typically no greater than 5 micrometers as measured using, for example, a sedimentation analyzer. Suitable FAS glasses will be familiar to those skilled in the art, and are available from a wide variety of commercial sources, and many are found in currently available glass ionomer cements such as those commercially available under the trade designations VITREMER, VITREBOND, RELY X LUTING CEMENT, RELY X LUTING PLUS CEMENT, PHOTAC-FIL QUICK, KETAC-MOLAR, and KETAC-FIL PLUS (3M ESPE Dental Products, St. Paul, Minn.), FUJI II LC and FUJI IX (G-C Dental Industrial Corp., Tokyo, Japan) and CHEMFIL Superior (Dentsply International, York, Pa.). Mixtures of fillers can be used if desired.

The surface of the filler particles can also be treated with a coupling agent in order to enhance the bond between the filler and the resin. The use of suitable coupling agents include gamma-methacryloxypropyltrimethoxysilane, gamma-mercaptopropyltriethoxysilane, gamma-aminopropyltrimethoxysilane, and the like.

Other suitable fillers are disclosed in U.S. Pat. No. 6,387,981 (Zhang et al.) and U.S. Pat. No. 6,572,693 (Wu et al.) as well as International Publication Nos. WO 01/30305 (Zhang et al.), WO 01/30306 (Windisch et al.), WO 01/30307 (Zhang et al.), and WO 03/063804 (Wu et al.). Filler components described in these references include nanosized silica particles, nanosized metal oxide particles, and combinations thereof. Nanofillers are also described in U.S. patent application Ser. Nos. 10/847,781; 10/847,782; and 10/847,803; all three of which were filed on May 17, 2004.

Self-adhesive compositions of the present invention include at least 40% by weight, preferably at least 45% by weight, and more preferably at least 50% by weight filler, based on the total weight of the composition. For such embodiments, compositions of the present invention preferably include at most 90% by weight, more preferably at most 80% by weight, even more preferably at most 75% by weight filler, and most preferably at most 70% by weight filler, based on the total weight of the composition.

Optional Photobleachable Dye

In some embodiments, compositions of the present invention preferably have an initial color remarkably different than dental structures. Color is preferably imparted to the composition through the use of a photobleachable dye. The composition preferably includes at least 0.001% by weight photobleachable dye, and more preferably at least 0.002% by weight photobleachable dye, based on the total weight of the composition. The composition preferably includes at most 1% by weight photobleachable dye, and more preferably at most 0.1% by weight photobleachable dye, based on the total weight of the composition. The amount of photobleachable dye may vary depending on its extinction coefficient, the ability of the human eye to discern the initial color, and the desired color change.

The color formation and bleaching characteristics of the photobleachable dye varies depending on a variety of factors including, for example, acid strength, dielectric constant, polarity, amount of oxygen, and moisture content in the atmosphere. However, the bleaching properties of the dye can be readily determined by irradiating the composition and evaluating the change in color. Preferably, at least one photobleachable dye is at least partially soluble in a hardenable resin.

Exemplary classes of photobleachable dyes are disclosed, for example, in U.S. Pat. No. 6,331,080 (Cole et al.), U.S. Pat. No. 6,444,725 (Trom et al.), and U.S. Pat. No. 6,528,555 (Nikutowski et al.). Preferred dyes include, for example, Rose Bengal, Methylene Violet, Methylene Blue, Fluorescein, Eosin Yellow, Eosin Y, Ethyl Eosin, Eosin bluish, Eosin B, Erythrosin B, Erythrosin Yellowish Blend, Toluidine Blue, 4',5'-Dibromofluorescein, and combinations thereof.

The color change in the inventive compositions is initiated by light. Preferably, the composition's color change is initiated using actinic radiation using, for example, a dental curing light which emits visible or near infrared (IR) light for a sufficient amount of time. The mechanism that initiates the color change in the compositions of the invention may be separate from or substantially simultaneous with the hardening mechanism that hardens the resin. For example, a composition may harden when polymerization is initiated chemically (e.g., redox initiation) or thermally, and the color change from an initial color to a final color may occur subsequent to the hardening process upon exposure to actinic radiation.

The change in composition color from an initial color to a final color is preferably quantified by a color test. Using a color test, a value of $\Delta E^*$ is determined, which indicates the total color change in a 3-dimensional color space. The human eye can detect a color change of approximately 3 $\Delta E^*$ units in normal lighting conditions. The dental compositions of the present invention are preferably capable of having a color change, $\Delta E^*$, of at least 20; more preferably, $\Delta E^*$ is at least 30; most preferably $\Delta E^*$ is at least 40.

Optional Additives

Optionally, compositions of the present invention may contain solvents (e.g., alcohols (e.g., propanol, ethanol), ketones (e.g., acetone, methyl ethyl ketone), esters (e.g., ethyl acetate), and other nonaqueous solvents (e.g., dimethylformamide, dimethylacetamide, dimethylsulfoxide, 1-methyl-2-pyrrolidinone)).

If desired, the compositions of the invention can contain additives such as indicators, dyes, pigments, inhibitors, accelerators, viscosity modifiers, wetting agents, tartaric acid, chelating agents, buffering agents, stabilizers, and other similar ingredients that will be apparent to those skilled in the art. Additionally, medicaments or other therapeutic substances can be optionally added to the dental compositions. Examples include, but are not limited to, fluoride sources, whitening agents, anticaries agents (e.g., xylitol), remineralizing agents (e.g., calcium phosphate compounds), enzymes, breath fresheners, anesthetics, clotting agents, acid neutralizers, chemotherapeutic agents, immune response modifiers, thixotropes, polyols, anti-inflammatory agents, antimicrobial agents, antifungal agents, agents for treating xerostomia, desensitizers, and the like, of the type often used in dental compositions. Combination of any of the above additives may also be employed. The selection and amount of any one such additive can be selected by one of skill in the art to accomplish the desired result without undue experimentation.

Diluents

In some specific embodiments of the present invention, an aqueous diluent (i.e., a diluent including water) is applied to a dental structure surface to wet the surface. In some specific embodiments of the present invention, non-aqueous compositions (preferably, adhesive compositions) are mixed with a diluent for application to a dental structure surface (preferably a tooth surface).

In some embodiments, the aqueous diluent consists essentially of water or water in combination with a surfactant. The water can be distilled, deionized, or plain tap water. Generally, deionized water is preferred. Suitable surfactants are described herein above.

In some embodiments, the aqueous diluent can include, for example, an acid sensitive dye, an antibacterial agent, a water soluble monomer, a pH adjuster agent, a buffer, a stabilizer, a surfactant, a fluoride anion, a fluoride releasing agent, or combinations thereof. Suitable acid-sensitive dyes include, for example, those disclosed in U.S. Provisional Application Ser. Nos. 60/600,558, filed Aug. 11, 2004, and 60/586,326, filed Jul. 8, 2004.

For embodiments in which the aqueous diluent is mixed with non-aqueous compositions of the present invention, the amount of diluent should be sufficient to provide adequate handling and mixing properties and to permit the transport of ions, particularly in the filler-acid reaction. Preferably, water represents at least 2% by weight, and more preferably at least 5% by weight, of the total weight of ingredients used to form the composition. Preferably, water represents no greater than 90% by weight, and more preferably no greater than 80% by weight, of the total weight of ingredients used to form the composition.

Methods of Use

Self-adhesive compositions of the present invention can be used to promote the adhesion of dental materials to dental structures. Exemplary dental materials include, but are not limited to, dental restoratives, orthodontic appliances, and orthodontic adhesives. Compositions of the present invention can be the dental restorative or the orthodontic adhesive. Dental restoratives include, for example, composites, fillings, sealants, inlays, onlays, crowns, and bridges. Orthodontic appliances include, for example, brackets; buccal tubes; bands; cleats; buttons; lingual retainers; lingual bars; bite blockers; crowns used for connection to a Herbst appliance; attachment devices for use with tooth positioners and other removable appliances such as those described, for example, in U.S. Pat. No. 6,309,215 (Miller et al.) and pending U.S. patent application Ser. No. 10/865,649 filed Jun. 10, 2004 (Cinader et al.); and other devices capable of changing or retaining tooth position. Orthodontic appliances can optionally be precoated with an orthodontic adhesive. Orthodontic adhesives can be uncured or cured (e.g., as encountered in indirect bonding methods).

In some embodiments, the self-adhesive compositions are hardened (e.g., polymerized by conventional photopolymerization and/or chemical polymerization techniques) prior to applying the dental material. In other embodiments, the self-adhesive compositions are hardened (e.g., polymerized by conventional photopolymerization and/or chemical polymerization techniques) after applying the dental material. It is significant if the composition can be formulated to promote adhesion to both enamel and dentin. It is also particularly significant if the composition can be formulated to function as the etchant, primer, adhesive, and restorative material (or orthodontic adhesive) for both enamel and dentin.

Suitable photopolymerizable compositions that can be used as dental materials and dental adhesive compositions in methods of the present invention can include epoxy resins (which contain cationically active epoxy groups), vinyl ether resins (which contain cationically active vinyl ether groups), ethylenically unsaturated compounds (which contain free radically active unsaturated groups, e.g., acrylates and methacrylates), and combinations thereof. Also suitable are polymerizable materials that contain both a cationically active functional group and a free radically active functional group in a single compound. Examples include epoxy-functional (meth)acrylates.

Self-adhesive compositions of the present invention can optionally include surfactants, solvents, and other additives. Various combinations of the components described herein can be used in the self-adhesive compositions of the present invention.

Certain preferred non-aqueous self-adhesive compositions (preferably, adhesives) (i.e., including less than 1% by weight water in the composition) of the present invention have enhanced chemical stability. That is, they have, for example, a room-temperature shelf-life stability of at least 1 year, and preferably at least 2 years. Additionally, such non-aqueous self-adhesive compositions may be applied directly to a wet dental structure surface (preferably a tooth surface). Alternatively, preferred non-aqueous self-adhesive compositions may be mixed (e.g., on a brush tip) with a diluent (e.g., water or water in combination with a surfactant) prior to applying to a wet or dry dental structure surface (preferably a tooth surface).

For embodiments of the present invention wherein the self-adhesive composition is non-aqueous, it is generally important that water be present on the structure surface at the time of treatment to achieve effective etching activity on a dental structure surface. This objective of having water present on the structure surface can be achieved by a variety of techniques and methods. Briefly, several typical methods are listed:

A first method is for the practitioner to leave the structure surface wet with water after rinsing, and therefore, eliminate or partially eliminate a typical drying step before structure treatment. A non-aqueous, self-adhesive composition can than be applied to the structure surface and cured using conventional methods.

A second method ("wet-brush" technique) is to sequentially dip a dental applicator into an aqueous diluent (e.g. water or water plus one or more additives), and then mix the wet brush with a non-aqueous, self-adhesive composition (e.g., a self-etching adhesive). The resulting aqueous mixture can than be applied to the structure surface and cured using conventional methods.

A third method is to sequentially treat a dry dental structure surface with an aqueous diluent (e.g. water or water plus one or more additives), followed by the application of a non-aqueous, self-adhesive composition. The resulting treated surface can then be further treated and cured using conventional methods.

Methods of bonding a dental material to a dental structure surface preferably result in a bond to enamel or dentin (or preferably both), of at least 0.7 MPa, more preferably at least 1.5 MPa, and most preferably at least 2 MPa, using the test method described in the Examples.

Objects and advantages of this invention are further illustrated by the following examples, but the particular materials and amounts thereof recited in these examples, as well as other conditions and details, should not be construed to unduly limit this invention. Unless otherwise indicated, all parts and percentages are on a weight basis, all water is deionized water, and all molecular weights are weight average molecular weight.

EXAMPLES

Test Methods

Adhesion to Enamel or Dentin Test Method

Adhesive strength to enamel or dentin for a given test sample was evaluated by the following procedure.

For each test sample, five freshly extracted bovine teeth of similar age and appearance were frozen after receipt and defrosted before use. (Storage time was approximately 1-2 weeks.) After defrosting each tooth, excess bovine meat was removed, the root was removed and the pulp drawn. Trimming was carried out to expose either dentin or enamel, and the resulting surface polished with wet silicon paper (320 grid/P400).

The polished tooth was then embedded in soft putty and the exposed surface fit with a wax mold (cylindrical die; hole diameter was 6.0 mm; bonding area was 28.3 mm$^2$) using double-sided adhesive tape. The exposed surface was rewet, air-dried, and then treated with the test sample composite for 20 seconds using a rubbing motion. The composite was then cured for 20 seconds using an ELIPAR TRILIGHT light gun, 800 mW/cm$^2$ (3M ESPE, St. Paul, Minn.). The wax mold was removed and a silanized screw was adhered to the cured composite using the Rocatec/Sinfony System (3M ESPE). Placement in the Visio Beta light curing device throughout curing of the composite was for 7 minutes.

The composite test sample assemblies were stored for 24 hours at 36° C. and 100% relative humidity before subjected to the Tensile Bond Strength Test (Zwick Instrument, Model No. Z010, Zwick Company, Ulm, Germany) with a crosshead speed of 1 mm/minute.

Each reported value (in units of MPa) of adhesion to enamel or adhesion to dentin represents the average of the 5 tooth replicates.

Flexural Strength (FS) Test Method

Flexural Strength was measured according to the published Test Standard ISO 4049:2000.

Compressive Strength (CS) Test Method

Compression Strength was measured according to the published Test Standard ISO 9917-1: 2003.

Abbreviations, Descriptions, and Sources of Materials

| Abbreviation | Description and Source of Material |
|---|---|
| TEGDMA | Triethyleneglycol dimethacrylate (Sartomer, Exton, PA) |
| Procrylat | 2,2-Bis-4-(3-hydroxy-propoxy-phenyl)propane dimethacrylate (CAS 27689-2-9) |
| Kayamer PM2 | Bis(methacryloxyethyl) phosphate (Nippon Kayaku, Japan) |
| GDMA-P | Glycerol dimethacrylate phosphate . . . Prepared as described in J. Dent. Res., 35, 8466 (1956) . . . cited in EP 0 237 233 (Oxman) (Also, see Example 3 in International Publication WO 02/092021 (Hecht et al.)) |
| MH-P | Methacryloxyhexyl phosphate (See Starting Materials Preparations described herein) |
| MO-P | 8-Methacryloxyoctyl phosphate (See Starting Materials Preparations described herein) |
| MD-P | 10-Methacryloxydecyl phosphate (See Starting Materials Preparations described herein) |
| AEROSIL OX-50 | Fumed silica (Degussa, Germany) |
| Filler A | Compolute GP 0.3% sil silanated with GF 31 as described in U.S. Pat. No. 4,376,835 (Schmitt et al.) |
| Filler B | Sinfony GP 5% silanated with GF 31, average particle size less than 0.7 micrometers (Schott Electronics Packaging GmbH, Landshut, Germany) |
| Filler C | Si Nanocluster AFG 100 V50 4% sil (Prepared as described in Example 1A of U. S. Publication No. 2003/0181541 (Wu et al.) |
| Filler D | Silane-treated zirconia-silica (Zr-Si) filler prepared as described in U.S. Pat. No. 4,503,169 (Randklev) |
| GF-31 | Trimethoxy-silyl-propoxy-methacrylic acid ester (WackerChemie GmbH, Burghausen, Germany) |
| Butyl BAP | Butyl phosphinoxide initiator (Prepared as described in EP Patent No. 0 184 095 (Ellrich et al.) |
| BHT | 2,6-Di-tert-butyl-4-methylphenol (Sigma-Aldrich, St. Louis, MO) |
| DDSS | Dodecyl sulfate sodium salt (Sigma-Aldrich) |

Starting Materials Preparations

6-Methacryloxyhexyl Phosphate (MH-P)

6-Hydroxyhexyl Methacrylate Synthesis:

1,6-Hexanediol (1000.00 g, 8.46 mol, Sigma-Aldrich) was placed in a 1-liter 3-neck flask equipped with a mechanical stirrer and a narrow tube blowing dry air into the flask. The solid diol was heated to 90° C., at which temperature all the solid melted. With continuous stirring, p-toluenesulfonic acid crystals (18.95 g, 0.11 mol) followed by BHT (2.42 g, 0.011 mol) and methacrylic acid (728.49.02 g, 8.46 mol). Heating at 90° C. with stirring was continued for 5 hours during which time vacuum was applied using tap water aspirator for 5-10 minutes after each half-hour reaction time. The heat was turned off and the reaction mixture was cooled to room temperature. The viscous liquid obtained washed with 10% aqueous sodium carbonate twice (2×240 ml), followed by washing with water (2×240 ml), and finally with 100 ml of saturated NaCl aqueous solution. The obtained oil was dried using anhydrous Na$_2$SO$_4$ then isolated by vacuum filtration to give 1067 g (67.70%) of 6-hydroxyhexyl methacrylate, a yellow oil. This desired product was formed along with 15-18% of 1,6-bis(methacryloyloxyhexane). Chemical characterization was by NMR analysis.

6-Methacryloxyhexyl Phosphate (MH-P) Synthesis:

A slurry was formed by mixing $P_4O_{10}$ (178.66 g, 0.63 mol) and methylene chloride (500 ml) in a 1-liter flask equipped with a mechanical stirrer under $N_2$ atmosphere. The flask was cooled in an ice bath (0-5° C.) for 15 minutes. With continuous stirring, 6-hydroxyhexyl methacrylate (962.82 g, which contained 3.78 mol of the mono-methacrylate, along with its dimethacrylate by-product as described above) was added to the flask slowly over 2 hours. After complete addition, the mixture was stirred in the ice bath for 1 hour then at room temperature for 2 hours. BHT (500 mg) was added, and then the temperature was raised to reflux (40-41° C.) for 45 minutes. The heat was turned off and the mixture was allowed to cool to room temperature. The solvent was removed under vacuum to afford 1085 g (95.5%) of 6-Methacryloxyhexyl Phosphate (MH-P) as a yellow oil. Chemical characterization was by NMR analysis.

8-Methacryloxyoctyl Phosphate (MO-P)

8-Methacryloxyoctyl Phosphate was prepared by the general procedure described above for 6-Methacryloxyhexyl Phosphate, except that 1,8-octanediol was used in place of 1,6-hexanediol. Chemical characterization of the final product was by NMR analysis.

10-Methacryloxydecyl Phosphate (MD-P)

10-Methacryloxydecyl Phosphate was prepared by the general procedure described above for 6-Methacryloxyhexyl Phosphate, except that 1,10-decanediol was used in place of 1,6-hexanediol. Chemical characterization of the final product was by NMR analysis.

Examples 1-5 and Comparative Examples 1-3

Examples 1-5 and Comparative Examples 1-3 were prepared by combining the components in Table 1 according to the following general procedure: The curable ethylenically unsaturated components were mixed to form a uniform phase. Subsequently, the initiator system components were added with mixing to a homogeneous state. Finally, the fillers and other components were added and thoroughly dispersed to afford a homogeneous paste composition.

Examples 1-5 and Comparative Examples 1-3 were evaluated for Adhesion to Dentin, Adhesion to Enamel, Flexural Strength, and Compressive Strength according to the Test Methods described herein and the results are provided in Table 1. It is observed from Table 1 that none of the Comparative Examples provided both good adhesion to a tooth surface and high mechanical values. (It is desirable to have adhesion at least 3.0 MPa, flexural strength at least 100 MPa and compressive strength at least 250 MPa). In contrast, all the Examples of the present invention (Examples 1-5) provided good adhesion to a tooth surface (either dentin, enamel, or both) and high mechanical values.

TABLE 1

Components (% by Weight) in Examples 1-5 and Comparative Examples (CE) 1-3

| Components | Example 1 | Example 2 | Example 3 | Example 4 | Example 5 | CE 1 | CE 2 | CE 3 |
|---|---|---|---|---|---|---|---|---|
| Filler A | 37.9 | 0 | 0 | 0 | 0 | 37.9 | 37.9 | 37.9 |
| Filler B | 28.9 | 0 | 0 | 0 | 0 | 28.9 | 28.9 | 28.9 |
| Filler C | 0 | 61.8 | 0 | 0 | 0 | 0 | 0 | 0 |
| Filler D | 0 | 0 | 68.0 | 68.0 | 68.0 | 0 | 0 | 0 |
| TEGDMA | 8.8 | 10.2 | 5.2 | 5.2 | 5.2 | 8.8 | 4.5 | 8.8 |
| Procrylat | 6.4 | 7.4 | 7.3 | 7.3 | 7.3 | 6.4 | 6.3 | 6.4 |
| Kayamer PM2 | 6.3 | 7.3 | 11.5 | 11.5 | 11.5 | 12.5 | 0 | 0 |
| GDMA-P | 0 | 0 | 3.8 | 3.8 | 3.8 | 0 | 16.4 | 0 |
| MH-P | 6.3 | 7.3 | 3.8 | 0 | 0 | 0 | 0 | 12.5 |
| MO-P | 0 | 0 | 0 | 3.8 | 0 | 0 | 0 | 0 |
| MD-P | 0 | 0 | 0 | 0 | 3.8 | 0 | 0 | 0 |
| AEROSIL OX-50 | 5.2 | 5.2 | 0 | 0 | 0 | 5.2 | 5.2 | 5.2 |
| Butyl BAP | 0.2 | 0.4 | 0.3 | 0.3 | 0.3 | 0.2 | 0.7 | 0.2 |
| BHT | 0.1 | 0.1 | 0.1 | 0.1 | 0.1 | 0.1 | 0.1 | 0.1 |
| DDSS | 0 | 0.5 | 0 | 0 | 0 | 0 | 0 | 0 |
| TOTAL: | 100 | 100 | 100 | 100 | 100 | 100 | 100 | 100 |
| EVALUATION RESULTS: | | | | | | | | |
| Adhesion to Dentin (MPa) | 3.0 | 0.7 | 2.8 | 2.9 | 1.9 | 2.5 | 0 | 0 |
| Adhesion to Enamel (MPa) | 6.1 | 3.8 | 5.5 | 8.1 | 10.6 | 4.1 | 0 | 2.7 |
| Flexural Strength (MPA) | 116 | 105 | 115 | 92 | 108 | 79 | 138 | 76 |
| Compressive Strength (MPA) | 251 | 307 | 351 | 329 | 331 | 264 | 301 | 204 |

Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A self-adhesive composition comprising:
   a first compound comprising at least one (meth)acryloxy group and at least one —O—P(O)(OH)$_x$ containing group, wherein x=1 or 2, and wherein the at least one —O—P(O)(OH)$_x$ containing group and the at least one (meth)acryloxy group are linked together by a C1-C3 hydrocarbon group;
   a second compound comprising at least one (meth)acryloxy group and at least one —O—P(O)(OH)$_x$ containing group, wherein x=1 or 2, and wherein the at least one —O—P(O)(OH)$_x$ containing group and the at least one (meth)acryloxy group are linked together by a C5-C12 hydrocarbon group;
   an ethylenically unsaturated compound without acid functionality;
   an initiator system; and
   a filler, wherein the self-adhesive composition is non-aqueous and comprises at least 40% by weight filler, with the proviso that the self-adhesive composition does not comprise fluoroaluminosilicate glass.

2. The self-adhesive composition of claim 1 wherein the at least one —O—P(O)(OH)$_x$ containing group and the at least one (meth)acryloxy group of the first compound are linked together by a C2 hydrocarbon group.

3. The self-adhesive composition of claim 1 wherein the at least one —O—P(O)(OH)$_x$ containing group and the at least one (meth)acryloxy group of the second compound are linked together by a C6-C10 hydrocarbon group.

4. The self-adhesive composition of claim 1 wherein the at least one —O—P(O)(OH)$_x$ containing group and the at least one (meth)acryloxy group of the second compound are linked together by a C6 hydrocarbon group.

5. The self-adhesive composition of claim 1 wherein the ethylenically unsaturated compound without acid functionality comprises at least two ethylenically unsaturated groups per molecule.

6. The self-adhesive composition of claim 5 wherein the at least two ethylenically unsaturated groups are selected from the group consisting of acryloxy groups, methacryloxy groups, vinyl groups, styryl groups, and combinations thereof.

7. The self-adhesive composition of claim 5 wherein the ethylenically unsaturated compound without acid functionality comprises at least two methacryloxy groups per molecule.

8. The self-adhesive composition of claim 1 wherein the composition is an orthodontic adhesive.

9. The self-adhesive composition of claim 8 wherein the orthodontic adhesive is provided as a precoated orthodontic appliance.

10. The self-adhesive composition of claim 9 wherein the orthodontic appliance is selected from the group consisting of a bracket, a buccal tube, a band, a cleat, a button, a lingual retainer, a lingual bar, a bite blocker, a crown used for connection to a Herbst appliance, an attachment device for use with a tooth positioner, an attachment device for use with a removable appliance, and combinations thereof.

11. A self-adhesive composition comprising:
a compound of Formula I

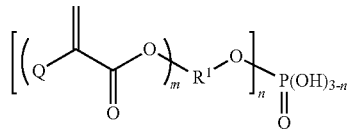

wherein m and n are each independently 1 or 2, Q is hydrogen or a methyl group, and R$^1$ is a C1-C3 hydrocarbon group;
a compound of Formula II

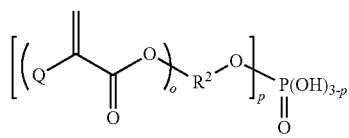

wherein o and p are each independently 1 or 2, Q is hydrogen or a methyl group, and R$^2$ is a C5-C12 hydrocarbon group;
an ethylenically unsaturated compound without acid functionality;
an initiator system; and
a filler,
wherein the self-adhesive composition is non-aqueous and comprises at least 40% by weight filler, with the proviso that the self-adhesive composition does not comprise fluoroaluminosilicate glass.

12. The self-adhesive composition of claim 11 wherein R$^1$ is a C2 hydrocarbon group.

13. The self-adhesive composition of claim 11 wherein R$^2$ is a C6-C10 hydrocarbon group.

14. The self-adhesive composition of claim 11 wherein R$^2$ is a C6 hydrocarbon group.

15. A method of restoring a dental structure, the method comprising:
applying a self-adhesive composition according to claim 1 to a dental structure surface; and
hardening the self-adhesive composition under conditions effective to form a bond between the hardened composition and the dental structure.

16. The method of claim 15 wherein the dental structure surface comprises enamel, dentin, or cementum.

17. The method of claim 15 wherein the dental structure surface is unetched prior to applying the self-adhesive composition.

18. The method of claim 15 wherein the dental structure surface is wet prior to applying the self-adhesive composition.

19. The method of claim 18 further comprising applying an aqueous diluent to an unetched dental structure surface to provide the wet, unetched dental structure surface.

20. The method of claim 19 wherein the aqueous diluent further comprises an acid sensitive dye, an antibacterial agent, a water soluble monomer, a pH adjuster agent, a buffer, a stabilizer, a surfactant, a fluoride anion, a fluoride releasing agent, or combinations thereof.

21. A method of adhering an orthodontic appliance to a tooth, the method comprising:
providing a self-adhesive composition comprising:
a first compound comprising at least one (meth)acryloxy group and at least one —O—P(O)(OH)$_x$ containing group, wherein x=1 or 2, and wherein the at least one —O—P(O)(OH)$_x$ containing group and the at least one (meth)acryloxy group are linked together by a C1-C4 hydrocarbon group;
a second compound comprising at least one (meth)acryloxy group and at least one —O—P(O)(OH)$_x$ containing group, wherein x=1 or 2, and wherein the at least one —O—P(O)(OH)$_x$ containing group and the at least one (meth)acryloxy group are linked together by a C5-C12 hydrocarbon group;
an ethylenically unsaturated compound without acid functionality;
an initiator system; and
a filler,
wherein the self-adhesive composition is non-aqueous and comprises at least 40% by weight filler, with the proviso that the self-adhesive composition does not comprise fluoroaluminosilicate glass;
applying the self-adhesive composition to a tooth surface under conditions effective to cause the self-adhesive composition to etch the tooth surface;
applying an orthodontic appliance to the tooth surface having the self-adhesive composition applied thereon; and
hardening the self-adhesive composition under conditions effective to form a bond between the orthodontic appliance and the tooth.

22. The method of claim 21 wherein the orthodontic appliance is selected from the group consisting of a bracket, a buccal tube, a band, a cleat, a button, a lingual retainer, a lingual bar, a bite blocker, a crown used for connection to a Herbst appliance, an attachment device for use with a tooth positioner, an attachment device for use with a removable appliance, and combinations thereof.

23. A method of adhering an orthodontic appliance to a tooth, the method comprising:
applying an orthodontic appliance having a self-adhesive composition thereon, to a wet tooth surface under conditions effective to cause the self-adhesive composition to etch the tooth surface; and
hardening the self-adhesive composition under conditions effective to form a bond between the orthodontic appliance and the tooth,
wherein the self-adhesive composition comprises:
a first compound comprising at least one (meth)acryloxy group and at least one $-O-P(O)(OH)_x$ containing group, wherein x=1 or 2, and wherein the at least one $-O-P(O)(OH)_x$ containing group and the at least one (meth)acryloxy group are linked together by a C1-C4 hydrocarbon group;
a second compound comprising at least one (meth)acryloxy group and at least one $-O-P(O)(OH)_x$ containing group, wherein x=1 or 2, and wherein the at least one $-O-P(O)(OH)_x$ containing group and the at least one (meth)acryloxy group are linked together by a C5-C12 hydrocarbon group;
an ethylenically unsaturated compound without acid functionality;
an initiator system; and
a filler,
wherein the self-adhesive composition is non-aqueous and comprises at least 40% by weight filler, with the proviso that the self-adhesive composition does not comprise fluoroaluminosilicate glass.

24. The method of claim 23 further comprising applying the self-adhesive composition to an orthodontic appliance to provide the orthodontic appliance having the self-adhesive composition thereon.

25. The method of claim 23 wherein the orthodontic appliance having the self-adhesive composition thereon is provided as a precoated orthodontic appliance having the self-adhesive composition thereon.

26. The method of claim 23 wherein the orthodontic appliance is selected from the group consisting of a bracket, a buccal tube, a band, a cleat, a button, a lingual retainer, a lingual bar, a bite blocker, a crown used for connection to a Herbst appliance, an attachment device for use with a tooth positioner, an attachment device for use with a removable appliance, and combinations thereof.

* * * * *